US006528047B2

(12) United States Patent
Arif et al.

(10) Patent No.: US 6,528,047 B2
(45) Date of Patent: Mar. 4, 2003

(54) ODOR ABSORPTION AND DEODORIZATION

(75) Inventors: Shoaib Arif, Dublin, OH (US); Raushanah Rinehart, Blacklick, OH (US)

(73) Assignee: Goldschmidt Chemical Corporation, Hopewell, VA (US)

( * ) Notice: Subject to any disclaimer, the term of this patent is extended or adjusted under 35 U.S.C. 154(b) by 53 days.

(21) Appl. No.: 09/837,790

(22) Filed: Apr. 18, 2001

(65) Prior Publication Data

US 2003/0007945 A1 Jan. 9, 2003

(51) Int. Cl.[7] .............. A61L 9/01; A61K 7/32; A61K 7/36; A61K 7/00
(52) U.S. Cl. .......... 424/76.1; 424/65; 424/67; 424/401
(58) Field of Search .............. 424/76.1, 65, 67, 424/401, 420

(56) References Cited

U.S. PATENT DOCUMENTS

| | | |
|---|---|---|
| 4,968,496 A | 11/1990 | Rohe et al. |
| 5,593,670 A | 1/1997 | Trinh et al. |
| 5,668,097 A | 9/1997 | Trinh et al. |
| 5,714,137 A | 2/1998 | Trinh et al. |
| 5,783,544 A | 7/1998 | Trinh et al. |
| 5,939,060 A | 8/1999 | Trinh et al. |
| 5,942,217 A | 8/1999 | Woo et al. |
| 6,036,964 A * | 3/2000 | Guenin et al. .............. 424/401 |

FOREIGN PATENT DOCUMENTS

| | | |
|---|---|---|
| DE | 19728997 | 2/1998 |
| EP | 327927 | 8/1989 |

OTHER PUBLICATIONS

"Bindung von Geruchsemissionen bei Abwasser–, Abluft–und Kompostierungsanlagen, Teil I–Einführung in die Problematik", Von Heinz–Werner Hennig, et al., Chemiker–Zeilung, 110, Jahrgang No. 2, pp. 63–68 (1986) together with English language Abstract.

"Bindung von Geruchsemissionen bei Abwasser–, Abluft–und Kompostierungsanlagen Teil IV: Untersuchungen zum Wirkungsmechanismus der Osmogen–Bindung mit der selektiven Wirksubstanz Grillocin®", Von Heinz–Werner Hennig, et al., Fachgebiet Anorganische Chemie der Universität/GH Duisburg, Chemiker–Zeitung, 113, Jahrgang, No. 2, pp. 73–79, (1989), together with English language Abstract.

"Mechanism of the Odor–Absorption Effect of Zinc Ricinoleate. A molecular Dynamics Computer Simulation", H. Kuhn, et al., Journal of Surfactants and Detergents, vol. 3, No. 3, (Jul. 2000).

* cited by examiner

Primary Examiner—Thurman K. Page
Assistant Examiner—Blessing Fubara
(74) Attorney, Agent, or Firm—Scully, Scott, Murphy & Presser

(57) ABSTRACT

A water-soluble home care concentrate is provide which includes a blend of zinc ricinoleate; and at least one alkoxylated amine having the formula $R(nAO)_sNH_t$, wherein R is a saturated or unsaturated, linear or branched alkyl containing from 8 to 22 carbon atoms; AO is a $C_2$–$C_6$ alkoxylate; n is the number of moles of AO and is from 1 to 50; s=1, 2 or 3; t=0, 1 or 2; and the sum of s and t is 3. The present invention also relates to diluted formulations that include the inventive water-soluble concentrate and at a least one solvent such as water and/or a carboxylic acid that is capable of solubilizes the concentrated blend into a diluted formulation that contains about 20%, by weight, or greater activated zinc atoms therein which are capable of binding with malodor molecules. The present invention also provides home care formulations that include the inventive diluted formulation and at least one additional formulating agent such as a perfume, dye, surfactant and the like. Methods of forming the inventive water-soluble concentrate, diluted formulation and home care formulations are also provided in the present invention.

42 Claims, No Drawings

US 6,528,047 B2

ODOR ABSORPTION AND DEODORIZATION

FIELD OF THE INVENTION

The present invention relates to an odor absorbing concentrate, and more particularly to a water-soluble odor controlling concentrate that is based-upon zinc ricinoleate and at least one alkoxylated amine. When the water-soluble odor controlling concentrate of the present invention is solubilized by an appropriate solvent, the diluted form of the inventive concentrate exhibits enhanced odor absorbing and deodorizing capabilities because of the presence of a greater number of activated zinc atoms than prior art zinc ricinoleate-containing formulations. Because of the enhanced odor absorbing and deodorizing capabilities, the inventive concentrate and dilutable formulation can be employed in a wide variety of applications including, but not limited to: in carpet cleaners, bathroom cleaners, pet order removers, cat liter deodorizers, car refresheners, floor cleaners, spray deodorizers, food processing plant cleaners and in other like home care applications.

BACKGROUND OF THE INVENTION

It is widely known that malodors (i.e., undesirable odors) can be controlled and in some instances eliminated by utilizing a deodorizing method such as a masking process, an absorption process, an ozone deodorizing process, or a catalytic process which uses a catalytic material such as a metal oxide or enzyme.

Masking processes control malodors by vaporizing and dispersing an aromatic liquid or solid such as a perfume into the ambient containing the malodor. Thus, masking processes modify the malodor to a more pleasant character by superimposing a dominant, but more pleasant odorant into the ambient. One problem with conventional aromatic liquids and solids is that such compounds tend to evaporate over an extended period of time which may result in the return of the malodor.

Absorption processes control malodors by employing an absorbent such as activated carbon or the like which absorbs odor components from the ambient. Thus, in this process, the level of intensity of the malodor is constantly being reduced from the ambient thereby refreshing the ambient.

The ozone deodorizing process serves to decompose odor components with ozone and in catalytic processes the odor components are modified in some fashion by the catalyst being used. In typical catalytic processes, enzymes are employed as the deodorizers.

In many home care applications, malodor control and/or elimination is achieved mainly by using either a masking process or an absorption process since ozone and catalytic processes are generally not feasible.

Some commonly employed odor absorbents employed in home care applications are formulations that are based on bleach oxidizing agents, peroxides, bactericides which kill microorganisms, cyclodextrins, and/or zinc ricinoleate.

U.S. Pat. Nos. 5,593,670; 5,668,097; 5,714,137; 5,783,544; 5,939,060; and 5,942,217 disclose odor-absorbing formulations that are based on uncomplexed cyclodextrins. The uncomplexed cyclodextrins employed in these references have a unique shape and the physical-chemical property of the cavity enables the cyclodextrin to absorb organic molecules or parts of the organic molecule which can fit into the cavity.

Zinc ricinoleate is a waxy solid that is substantially insoluble in water. Despite the water insoluble nature of zinc ricinoleate, this compound tends to form strong bonds with malodor molecules containing nitrogen and sulfur atoms. In order for zinc ricinoleate to form bonds with malodor molecules, the zinc atoms need to be activated so as to expose their available reaction sites. Activation of zinc ricinoleate, and hence activation of the zinc atoms, is typically carried out by solubilizing the compound in water. Once in solution, the reaction sites on the zinc atoms are available to form bonds with nitrogen and sulfur atoms thereby binding the malodor and removing it from the ambient. Formulations based on zinc ricinoleate differ from formulations based on cyclodextrins, since zinc ricinoleate-containing formulations remove malodor molecules by a binding mechanism, whereas cyclodextrin-containing formulations remove malodor molecules via entrapment.

Solubilization of zinc ricinoleate in water is not however an easy task. Instead, special surfactants and solvents like amine oxides, betaine, triethylene glycol, sulfosuccinates and other like materials are typically employed to carry out the solubilization. Even when solubilization of zinc ricinoleate is successful, the resultant solubilized solution will contain only about 10% active material, i.e., activated zinc atoms. That is, a diluted solution, i.e., solubilized solution, containing 10% activated zinc ricinoleate and 90% surfactant or solvent is obtained.

Although formulations based on prior are zinc ricinoleate concentrates may be used in many home care applications, much of the zinc atoms present in prior art formulations are not activated therefore they will not form bonds with the nitrogen and sulfur atoms present in malodor molecules. Hence, much of the absorbing/deodorizing capability of prior art zinc ricinoleate formulations is not realized. Therefore, formulated products based on prior art solubilized zinc ricinoleate concentrates function well below their potential absorbing/deodorizing capability.

In view of the above mentioned problem with conventional solubilized zinc ricinoleate concentrates, there is a continued need for providing a new and improved solubilized zinc ricinoleate concentrate that contains more activated zinc atoms than is the case with prior art solubilized zinc ricinoleate concentrates.

SUMMARY OF THE INVENTION

The present invention relates to a water-soluble home care concentrate that exhibits a high capability of absorbing malodors from an ambient so as to refresh that ambient. The inventive water-soluble home care concentrate is based on a zinc ricinoleate/alkoxylated amine blend which when solubilized by an appropriate solvent provides a diluted formulation that contains about 20%, by weight, or greater activated zinc atoms.

Specifically, the inventive water-soluble home care concentrate comprises a blend of zinc ricinoleate and at least one alkoxylated amine having the formula $R(nAO)_sNH_t$, wherein R is a saturated or unsaturated, linear or branched alkyl containing from 8 to 22, preferably 12 to 18, carbon atoms; AO is a $C_2$–$C_6$, preferably $C_2$–$C_4$, alkoxylate; n is the number of moles of AO and is from 1 to 50, preferably 2–10; s=1, 2 or 3; t=0, 1 or 2; and the sum of s and t is 3.

The water-soluble concentrate of the present invention can be used in a wide variety of home care applications in which malodor reduction and/or elimination is required. For example, the inventive water-soluble concentrate can be employed in carpet cleaners, bathroom cleaners, pet order removers, cat liter deodorizers, car refresheners, floor cleaners, spray deodorizers, food processing plant cleaners and in other like home care applications.

In addition to providing a water-soluble concentrate, the present invention also provides a diluted formulation that comprises from about 1 to about 50 weight % of the inventive water-soluble concentrate; and from about 50 to 99 weight % of at least one solvent. The diluted formulation of the present invention contains about 20%, by weight, or greater, preferably 30% or greater, activated zinc atoms therein. Home care formulations including the inventive dilutable formulation remove malodor molecules via a binding mechanism, rather than entrapment of the malodor molecules within a cavity.

The at least one solvent employed in this aspect of the present invention includes, but is not limited to: water; carboxylic acids such as citric acid, maleic acid, succinic acid, propenoic acid, glycolic acid, acetic acid, lactate acid; salts of said carboxylic acids; and mixtures thereof. Preferred solvents are water, a mixture of water and citric acid, or a mixture of lactate acid and water. In the case of a solvent mixture of lactate acid and water, a 100% solubilized clear concentrate is provided.

Another aspect of the present invention relates to a method of preparing the above-mentioned water-soluble concentrate. Specifically, the inventive method that is employed in fabricating the aforementioned water-soluble concentrate comprises the steps of:

(a) providing a mixture of zinc ricinoleate and at least one alkoxylated amine having the formula $R(nAO)_sNH_t$, wherein R is a saturated or unsaturated, linear or branched alkyl containing from 8 to 22, preferably 12 to 18, carbon atoms; AO is a $C_2$–$C_6$, preferably $C_2$–$C_4$, alkoxylate; n is the number of moles of AO and is from 1 to 50, preferably 2–10; s=1, 2 or 3; t0, 1 or 2; and the sum of s and t is 3; and (b) heating the mixture to a temperature that is above the melting point of the zinc ricinoleate so as to provide a concentrated blend.

In yet another aspect of the present invention, a method for preparing a diluted formulation is provided. Specifically, this aspect of the present invention comprises the steps of:

(a) providing a concentrated zinc ricinoleate/alkoxylated amine blend; and (b) adding at least one solvent to said concentrated zinc ricinoleate/alkoxylated amine blend so as to provide a diluted formulation that contains about 20%, by weight, or greater activated zinc atoms therein.

DETAILED DESCRIPTION OF THE INVENTION

As stated above, the present invention relates to a water-soluble home care concentrate that is capable of reducing and/or eliminating malodors from an ambient containing the same. The term "ambient" as used herein denotes any atmosphere that a human olfactory system is capable of breathing and in which odors, including malodors, can be detected.

The first component of the inventive water-soluble concentrate is zinc ricinoleate which exists as a waxy solid that is substantially insoluble in water. The zinc ricinoleate employed in the present invention is commercially available under the tradename TEGO SORB PY 88 or it can be made using conventional processes well known in the art. For example, the zinc ricinoleate employed in the present invention may be made by reacting a zinc salt, i.e., $ZnCl_2$, with ricinoleic acid (i.e., an oily unsaturated hydroxy fatty acid $C_{18}H_{34}O_3$ that typically occurs in castor oil as a glyceride) and thereafter esterifying the resultant reaction product.

The second component of the inventive water-soluble concentrate is at least one alkoxylated amine having the formula $R(nAO)_sNH_t$, wherein R is a saturated or unsaturated, linear or branched alkyl containing from 8 to 22, preferably 12 to 18, carbon atoms; AO is a $C_2$–$C_6$, preferably $C_2$–$C_4$, alkoxylate; n is the number of moles of AO and is from 1 to 50, preferably 2–10; s=1, 2 or 3; t=0, 1 or 2; and the sum of s and t is 3.

Preferred alkoxylated amines that are employed in the present invention are $C_2$–$C_4$ alkoxylated coco or tallow amines that contain 2–10 moles of AO groups. Examples of such alkoxylated amines include VARONIC T210 which is an ethoxylated tallow amine (10 moles of ethoxylate, EO) supplied by Goldschmidt Chemical Corporation or VARONIC K-205 which is an ethoxylated coco amine (5 moles of ethoxylate, EO) supplied by Goldschmidt Chemical Corporation. Of these alkoxylated amines, it is highly preferred to employ ethoxylated coco amines such as VARONIC K-205 in the present invention.

The alkoxylated amine employed in the present invention serves two functions. First, the alkoxylated amine is employed in the present invention as a solubilizing agent for the zinc ricinoleate. That is, the alkoxylated amine employed in the present invention is capable of providing a highly activated zinc ricinoleate blend that can be completely solubilized (i.e., 100%) in water. The term "highly activated" as used herein denotes a zinc ricinoleate blend that is capable of providing a diluted formulation that contains 20%, by weight, or greater zinc atoms therein. In some preferred embodiments, the alkoxylated amine is capable of providing a diluted formulation that contains 30%, by weight, or greater zinc atoms therein. Note that this represents a significant advancement over the prior art wherein only 10% active material is solubilized.

The second function of the alkoxylated amine is that it provides enhanced cleaning properties to the formulations in which it is employed. Thus, formulations containing the inventive concentrate are not only capable of absorbing malodors from the ambient, but such formulations are also capable of providing enhanced cleaning properties. This combination of increased malodor absorption and cleaning is not found in any other formulation that contains zinc ricinoleate.

The inventive concentrate of the present invention is made by providing a blend of zinc ricinoleate and the at least one alkoxylated amine. The blend is fabricated by first adding the at least one alkoxylated amine to a solid of zinc ricinoleate. The addition of the at least one alkoxylated amine to zinc ricinoleate is carried out by conventional means well known in the art. For example, the addition may be carried out by the incremental addition of small quantities of alkoxylated amine into a vessel containing solid zinc ricinoleate with continuous stirring, or alternatively, the alkoxylated amine can be added all at once to the vessel containing solid ricinoleate with continuous stirring.

The amount of alkoxylated amine added to solid zinc ricinoleate will vary depending on the desired concentration of the resultant concentrate. Typically, in the present invention from about 150 to about 400 grams of alkoxylated amine is added to 100 grams of solid zinc ricinoleate, with from about 185 to about 300 grams of alkoxylated amine per 100 grams of solid zinc ricinoleate being more highly preferred.

After adding the alkoxylated amine to the solid zinc ricinoleate, the mixture is heated to a temperature above the melting point of zinc ricinoleate so as to form a concentrated blend which may be solubilized into a diluted formulation that contains 20%, by weight, or more activated zinc atoms. Specifically, the heating step is carried out at a temperature of from about 40° to about 80° C. for a time period of from about 10 to about 60 minutes. More preferably, this heating step is carried out at a temperature of from about 50° to about 70° C. for a time period of from about 20 to about 30 minutes. During the entire heating step, the admixture is typically stirred to ensure formation of a substantially homogeneous blend of the aforementioned components.

The above steps of addition and heating result in the formation of the inventive water-soluble concentrate which includes a blend of alkoxylated amine and zinc ricinoleate. Note that the entire process of fabricating the inventive water-soluble concentrate may be carried out under vacuum or in an inert gas ambient such as He, $N_2$ or Ar.

The inventive water-soluble concentrate may be packaged at this point of the present invention and shipped to a consumer for dilution and further formulation, or diluting and formulating may occur prior to packaging and shipment.

Insofar as dilution is concerned, a diluted formulation containing from about 20%, by weight, or greater activated zinc atoms therein is obtained by providing a concentrated zinc ricinoleate/alkoxylated amine blend using the above mentioned process and thereafter adding at least one solvent to said concentrated zinc ricinoleate/alkoxylated amine blend. The diluted formulation may also be referred to as a solubilized solution since the at least one solvent employed in the present invention is capable of completely solubilizes the inventive concentrate.

Specifically, the at least one solvent employed in this aspect of the present invention includes, but is not limited to: water; carboxylic acids such as citric acid, maleic acid, succinic acid, propenoic acid, glycolic acid, acetic acid, lactate acid; carboxylic acid salts; and mixtures thereof. Preferred solvents are water, a mixture of water and citric acid, or a mixture of lactate acid and water. The latter solvent is preferred in some instances since the combination of water and lactate acid provides a completely solubilizes zinc ricinoleate blend that is substantially clear.

The amounts of water-soluble concentrate and solvent employed in the present invention may vary depending on the attempted use of the diluted formulation. Typically, in the present invention from about 100 to about 10,000 ml of solvent is added to 100 ml of the inventive concentrate, with from about 1000 to about 3000 ml of solvent per 100 ml of the inventive concentrate being more highly preferred.

The addition of the at least one solvent to the water-soluble concentrate may be performed incrementally or by adding the whole quantity of solvent to the concentrate of the present invention. Dilution may be carried out with continuous stirring to ensure proper mixing of the ingredients. Additionally, the dilution may be carried out at room temperature or a slightly elevated temperature up to about 40° C. or less may be employed. Although dilution may be carried out in air, in some instances it is preferred to perform the dilution in an inert gas ambient.

The final diluted formulation of the present invention contains from about 1 to about 50 weight % of the water-soluble concentrate and from about 50 to about 99 weight % of the at least one solvent. More preferably, the diluted formulation contains from about 1 to about 10 weight % of water-soluble concentrate and from about 90 to about 99 weight % of said at least one solvent.

Notwithstanding the amounts used in making the diluted formulation, the diluted formulation contains 100% solubilized zinc ricinoleate that contains about 20% or greater activated zinc atoms therein. Moreover, the diluted formulation of the present invention has a viscosity of from about 100 to about 5000 cps, with a viscosity of from about 300 to about 1000 cps being more highly preferred.

The diluted water-soluble concentrate provided above which contains 20% or more activated zinc atoms therein may be used as is in some odor absorption/cleaning applications, or the diluted concentrate may be further formulated into various formulations that can be employed in a variety of home care applications. When additional formulation is employed, conventional ingredients that are typically present in the specific home care product may be employed. For example, conventional surfactants including anionic surfactants, ionic surfactants, amphoteric surfactants, zwitterionic surfactants or any combinations or mixtures thereof may be employed.

In additional to surfactants, the diluted water-soluble concentrate of the present invention may be used with conventional solvents, dyes, preservatives, emulsifying agents, perfumes, antibacterial agents, thickeners, conditioners, antistatic agents, silicone surfactants, and other like ingredients that are typically present in conventional home care formulations. Mixtures and/or combinations of the aforementioned additional formulating agents may also be employed in the present invention. The amounts of the additional formulating agents that may be employed in the present invention are within ranges that are well known to those skilled in the art and further formulating is performed using processes that are also well known in the art.

The following provides some suggested formulation guides for specific home care applications Note the term Inventive Concentrate denotes a blend of 30% zinc ricinoleate and 70% Varonic K-205):

| Ingredient | % w/w |
|---|---|
| I. General Purpose Odor Absorber Spray | |
| Water, deionized | 98.2 |
| Inventive Concentrate | 1.6 |
| Citric Acid | 0.2 |
| II. Carpet Shampoo with Odor Absorber | |
| Water, deionized | 83.9 |
| Inventive Concentrate | 3.0 |
| SLS 30% (i.e., sodium lauryl sulfate 30%) | 10.0 |
| Varamide 128-T (i.e., cocoamide diethanolamine) | 2.0 |
| Citric Acid | 0.5 |
| Triethanolamine | 0.6 |
| III. Toilet Bowl Cleaner with Odor Absorber | |
| Water, deionized | 94.5 |
| Inventive Concentrate | 5.0 |
| Citric Acid | 0.5 |
| IV. Bathroom Tub & Tile Cleaner with Odor Absorber | |
| Water, deionized | 94.0 |
| Inventive Concentrate | 5.0 |
| Citric Acid | 1.0 |
| V. Kitchen Cleaner & Degreaser with Odor Absorber | |
| Water, deionized | 96.2 |
| Inventive Concentrate | 3.3 |
| Citric Acid | 0.5 |

The following are some additional formulations that can include the inventive water-soluble concentrate:

| Ingredients | % w/w |
|---|---|
| Carpet Shampoo-1 | |
| Water | 88.94% |
| Standapol WAQ Special (i.e., a sodium lauryl sulfate) | 5.0% |
| Hamposyl L-30 (i.e., a sodium lauroyl sarcosinate) | 3.0% |
| Inventive Concentrate | 2.0% |
| Citric Acid | 0.5% |
| Triethanolamine | 0.56% |
| Dyes, preservatives | Q.S. |
| Total | 100 |
| Carpet Shampoo-2 | |
| Water | 83.85% |
| Standapol WAQ Special | 10.0% |
| Inventive Concentrate | 3.0% |
| Witcamide 128-T (i.e., a cocoamide diethanolamine) | 2.0% |
| Citric Acid | 0.5% |
| Triethanolamine | 0.65% |
| Dyes, preservatives | Q.S. |
| Total | 100 |
| Carpet Shampoo-3 | |
| Water | 85.64% |
| Hamposyl L-30 | 10.0% |
| Inventive Concentrate | 2.5% |
| Accusol 445 N (i.e., a polyacrylate) | 1.5% |
| Citric Acid | 0.36% |
| Dyes, preservatives | Q.S. |
| Total | 100 |
| Carpet Extraction Cleaner-1 | |
| Water | 96.5% |
| Rewoteric AM V (i.e., a sodium capryloamphoacetate) | 3.0% |
| Inventive Concentrate | 0.5% |
| Dyes, preservatives | Q.S. |
| Total | 100 |
| Carpet Extraction Cleaner-2 | |
| Water | 92.5% |
| Tegotens DO (i.e., a decamine oxide) | 5.0% |
| Inventive Concentrate | 2.0% |
| Citric Acid | 0.5% |
| Dyes, preservatives | Q.S. |
| Total | 100 |
| Carpet Extraction Cleaner-3 | |
| Water | 96.5% |
| Inventive Concentrate | 3.0% |
| Citric Acid | 0.5% |
| Dyes, preservatives | Q.S. |
| Total | 100 |
| Bathroom Tub & Tile Cleaner-1 | |
| Water | 94.0% |
| Inventive Concentrate | 5.0% |
| Citric Acid | 1.0% |
| Dyes, preservatives | Q.S. |
| Total | 100 |
| Bathroom Tub & Tile Cleaner-2 | |
| Water | 94.85% |
| Inventive Concentrate | 3.0% |
| Tetrapotassium Pyrophosphate | 2.0% |
| Citric Acid | 0.15% |
| Dyes, preservatives | Q.S. |
| Total | 100 |
| Bathroom Tub & Tile Cleaner-3 | |
| Water | 93.0% |
| Inventive Concentrate | 2.5% |
| Rewoteric AM V | 4.0% |
| Citric Acid | 0.5% |
| Dyes, preservatives | Q.S. |
| Total | 100 |
| Toilet Bowl Cleaner-1 | |
| Water | 94.5% |
| Inventive Concentrate | 5.0% |
| Citric Acid | 0.5% |
| Dyes, preservatives | Q.S. |
| Total | 100 |
| Toilet Bowl Cleaner-2 | |
| Water | 94.0% |
| Inventive Concentrate | 4.0% |
| Citric Acid | 2.0% |
| Dyes, preservatives | Q.S. |
| Total | 100 |
| Toilet Bowl Cleaner-3 | |
| Water | 80.0% |
| Inventive Concentrate | 5.0% |
| Phosphoric Acid | 10.0% |
| Rewoteric AM-TEG (i.e., a tallow hydroxy betaine) | 5.0% |
| Dyes, preservatives | Q.S. |
| Total | 100 |
| Pet Shampoo-1 | |
| Water | 63.6% |
| Standapol ES-2 (i.e., a sodium lauryl ether sulfate) | 20.0% |
| Inventive Concentrate | 3.3% |
| Rewoteric AMB-14 U (i.e., a cocoamidopropyl betaine) | 7.0% |
| Witcamide 128-T | 3.0% |
| Sodium Chloride | 2.0% |
| Citric Acid | 0.5% |
| Triethanolamine | 0.6% |
| Dyes, preservatives | Q.S. |
| Total | 100 |
| Pet Shampoo-2 | |
| Water | 56.7% |
| Rewoteric AM C (i.e., a sodium cocoamphoacetate) | 25.0% |
| Inventive Concentrate | 3.3% |
| Standapol T (i.e., a triethanolamine lauryl sulfate) | 15.0% |
| Dyes, preservatives | Q.S. |
| Total | 100 |
| Pet Shampoo-3 | |
| Water | 56.7% |
| Rewoteric AM 2 CW (i.e., a disodium cocoamphodiacetate) | 25.0% |
| Inventive Concentrate | 3.3% |
| Standapol ES-2 | 15.0% |
| Dyes, preservatives | Q.S. |
| Total | 100 |
| Liquid Hand Soap-1 | |
| Water | 57.5% |
| Witconate AOS (i.e., a sodium $C_{14-16}$ alpha olefin sulfonate) | 30.0% |
| Rewoteric AMB-14 U | 6.0% |
| Inventive Concentrate | 2.0% |
| Witcamide 128-T | 2.0% |
| Sodium Chloride | 2.0% |
| Citric Acid | 0.5% |

| Ingredients | % w/w |
|---|---|
| Dyes, preservatives | Q.S. |
| Total | 100 |
| Liquid Hand Soap-2 | |
| Water | 56.5% |
| Standapol ES-2 | 30.0% |
| Rewoteric AM C | |
| Inventive Concentrate | 3.0% |
| Citric Acid | 0.5% |
| Dyes, preservatives | Q.S. |
| Total | 100 |
| Liquid Hand Soap-3 | |
| Water | 54.0% |
| Standapol T | 15.0% |
| Rewoteric AM 2 CW | 25.0% |
| Inventive Concentrate | 2.5% |
| Sodium Chloride | 3.0% |
| Citric Acid | 0.5% |
| Dyes, preservatives | Q.S. |
| Total | 100 |
| Waterless Hand Cleaner-1 | |
| Water | 57.0% |
| Isopar M (Exxon; i.e., a mineral spirit) | 30.0% |
| Oleic Acid | 5.0% |
| Triethanolamine | 3.0% |
| Neodol 25-7 (i.e., an alcohol ethoxylate) | 2.0% |
| Inventive Concentrate | 3.0% |
| Dyes, preservatives | Q.S. |
| Total | 100 |
| Waterless Hand Cleaner-2 | |
| Water | 56.0% |
| D'Limonene | 30.0% |
| Natrosol 250 HR (i.e., a hydroxyethyl cellulose) | 1.0% |
| Polytergent SL-42 (i.e., an alcohol alkoxylate) | 2.0% |
| Inventive Concentrate | 3.0% |
| Oleic acid | 6.0% |
| Triethanolamine | 2.0% |
| Dyes, preservatives | Q.S. |
| Total | 100 |
| PH | 8.02 |
| Fabric Spray-1 | |
| Water | 62.5% |
| Inventive Concentrate | 1.0% |
| Isopropyl Alcohol | 35.0% |
| Citric acid | 0.5% |
| Carbopol 940 (i.e., a polyacrylic acid) | 1.0% |
| Dyes, preservatives | Q.S. |
| Total | 100 |
| PH | 5.09 |
| Floor Cleaner-1 | |
| Water | 89.0% |
| Inventive Concentrate | 2.5% |
| Tetrapotassium Pyrophosphate | 5.0% |
| Tegotens DO | 3.0% |
| Citric Acid | 0.5% |
| Dyes, preservatives | Q.S. |
| Total | 100 |
| Floor Cleaner-2 | |
| Water | 93.5% |
| Inventive Concentrate | 3.3% |
| Tegotens EC-11 (i.e., an alcohol alkoxylate) | 2.7% |
| Citric Acid | 0.5% |
| Dyes, preservatives | Q.S. |
| Total | 100 |
| Floor Cleaner-3 | |
| Water | 87.0% |
| Inventive Concentrate | 2.0% |
| Rewoteric AM V | 8.0% |
| Rewoteric AM KSF-40 (i.e., a sodium cocoamphopropionate) | 1.0% |
| Citric Acid | 1.0% |
| Triethanolamine | 1.0% |
| Dyes, preservatives | Q.S. |
| Total | 100 |
| PH | 6.07 |
| Kitchen Cleaner-1 | |
| Water | 96.2% |
| Inventive Concentrate | 3.3% |
| Citric Acid | 0.5% |
| Dyes, preservatives | Q.S. |
| Total | 100 |
| Kitchen Cleaner-2 | |
| Water | 94.9% |
| Tetrapotassium Pyrophosphate | 2.0% |
| Inventive Concentrate | 3.0% |
| Citric Acid | 0.1% |
| Dyes, preservatives | Q.S. |
| Total | 100 |
| Kitchen Cleaner-3 | |
| Water | 94.7% |
| Tetrapotassium Pyrophosphate | 0.5% |
| Inventive Concentrate | 3.3% |
| Dowanol DPM | 1.2% |
| Citric Acid | 0.152% |
| Dyes, preservatives | Q.S. |
| Total | 100 |
| PH | 8.21 |
| Sewage Treatment Plant Deodorizer | |
| Water | 84.25% |
| Inventive Concentrate | 15.0% |
| Citric Acid | 0.75% |
| Dyes, preservatives | Q.S. |
| Total | 100 |
| Car Interior Cleaner (Plastic Cleaner)-1 | |
| Water | 97.5% |
| Inventive Concentrate | 2.0% |
| Citric Acid | 0.5% |
| Dyes, preservatives | Q.S. |
| Total | 100 |
| Car Interior Cleaner (Plastic Cleaner)-2 | |
| Water | 87.5% |
| Inventive Concentrate | 2.0% |
| Isopropyl Alcohol | 10.0% |
| Citric Acid | 0.5% |
| Dyes, preservatives | Q.S. |
| Total | 100 |
| Car Interior Cleaner (Plastic Cleaner)-3 | |
| Water | 97.5% |
| Inventive Concentrate | 1.5% |
| Tegotens EC-11 | 0.5% |
| Citric Acid | 0.5% |
| Dyes, preservatives | Q.S. |
| Total | 100 |

| Ingredients | % w/w |
|---|---|
| Gelled Bathroom Cleaner-1 | |
| Water | 81.7% |
| Inventive Concentrate | 3.3% |
| Rewoteric AM-TEG | 7.0% |
| Phosphoric Acid | 5.0% |
| Sodium Chloride | 3.0% |
| Dyes, preservatives | Q.S. |
| Total | 100 |
| Gelled Bathroom Cleaner-2 | |
| Water | 83.2% |
| Inventive Concentrate | 3.3% |
| Standapol WAQ Special | 5.0% |
| Witcamide 128-T | 2.0% |
| Rewoteric AMB-14 U | 2.0% |
| Varox 1770 (i.e., a cocoamidopropylamine oxide) | 2.0% |
| Citric Acid | 0.5% |
| Sodium Chloride | 2.0% |
| Dyes, preservatives | Q.S. |
| Total | 100 |
| Food Processing Plant Cleaner | |
| Water | 90.2% |
| Inventive Concentrate | 3.3% |
| Tetrapotassium Pyrophosphate | 2.5% |
| Sodium Hydroxide | 2.5% |
| Sodium Metasilicate Pentahydrate | 1.0% |
| Citric Acid | 0.5% |
| Dyes, preservatives | Q.S. |
| Total | 100 |
| Furniture & Upholstery Cleaner (Upholstery Shampoo) | |
| Water | 91.5% |
| Inventive Concentrate | 3.0% |
| Petro BA Liquid (i.e., a naphltalene sulfonate) | 5.0% |
| Citric Acid | 0.5% |
| Dyes, preservatives | Q.S. |
| Total | 100 |
| Furniture & Upholstery Cleaner (Furniture Cleaner) | |
| Water | 91.5% |
| Inventive Concentrate | 2.0% |
| Tego Betaine 810 | 3.0% |
| Tegotens DO | 3.0% |
| Citric Acid | 0.5% |
| Dyes, preservatives | Q.S. |
| Total | 100 |
| Cat Litter | |
| Water | 63.6% |
| Inventive Concentrate | 33.4% |
| Citric Acid | 3.0% |
| Dyes, preservatives | Q.S. |
| Total | 100 |
| Animal Barn Spray | |
| Water | 92.9% |
| Inventive Concentrate | 6.6% |
| Citric Acid | 0.5% |
| Dyes, preservatives | Q.S. |
| Total | 100 |
| Animal Barn Floor Cleaner | |
| Water | 89.5% |
| Inventive Concentrate | 3.3% |
| Tetrapotassium Pyrophosphate | 5.0% |
| Rewoteric AM KSF-40 | 2.2% |
| Dyes, preservatives | Q.S. |

| Ingredients | % w/w |
|---|---|
| Total | 100 |
| Horse Shampoo-1 | |
| Water | 56.2% |
| Inventive Concentrate | 3.3% |
| Standapol ES-2 | 35.0% |
| Witcamide 128-T | 3.0% |
| Sodium Chloride | 2.0% |
| Citric Acid | 0.5% |
| Dyes, preservatives | Q.S. |
| Total | 100 |
| Horse Shampoo-2 | |
| Water | 46.7% |
| Inventive Concentrate | 3.3% |
| Witconate AOS | 40.0% |
| Rewoteric AMB-14 U | 5.0% |
| Witcamide 128-T | 2.5% |
| Citric Acid | 0.5% |
| Sodium Chloride | 2.0% |
| Dyes, preservatives | Q.S. |
| Total | 100 |
| Horse Shampoo-3 | |
| Water | 56.2% |
| Inventive Concentrate | 3.3% |
| Standapol T | 20.0% |
| Rewoteric AM C (i.e., a sodium cocoamphoacetate) | 20.0% |
| Citric Acid | 0.5% |
| Dyes, preservatives | Q.S. |
| Total | 100 |
| Industrial Laundry Prespotter-1 | |
| Water | 93.5% |
| Inventive Concentrate | 3.3% |
| Tegotens EC-11 | 2.7% |
| Citric Acid | 0.5% |
| Dyes, preservatives | Q.S. |
| Total | 100 |
| Industrial Laundry Prespotter-2 | |
| Water | 92.7% |
| Inventive Concentrate | 3.3% |
| Rewoteric AM KSF-40 | 1.5% |
| Varox 365 (i.e., a lauramine oxide) | 2.0% |
| Citric Acid | 0.5% |
| Dyes, preservatives | Q.S. |
| Total | 100 |
| Industrial Laundry Prespotter-3 | |
| Water | 93.5% |
| Inventive Concentrate | 6.0% |
| Citric Acid | 0.5% |
| Dyes, preservatives | Q.S. |
| Total | 100 |
| Dishwashing Detergent-1 | |
| Water | 56.2% |
| Calsoft L-40 (i.e., a linear alkyl benzene sulfonate) | 20.0% |
| Standapol ES-2 | 20.0% |
| Inventive Concentrate | 3.3% |
| Citric Acid | 0.5% |
| Dyes, preservatives | Q.S. |
| Total | 100 |
| Dishwashing Detergent-2 | |
| Water | 56.2% |
| Inventive Concentrate | 3.3% |
| Standapol T | 20.0% |

| Ingredients | % w/w |
|---|---|
| Rewoteric AM KSF-40 | 20.0% |
| Citric Acid | 0.5% |
| Dyes, preservatives | Q.S. |
| Total | 100 |
| Dishwashing Detergent-3 | |
| Water | 56.2% |
| Calsoft L-40 | 20.0% |
| Witconate AOS | 20.0% |
| Inventive Concentrate | 3.3% |
| Citric Acid | 0.5% |
| Dyes, preservatives | Q.S. |
| Total | 100 |
| Diaper Pail Spray-1 | |
| Water | 94.5% |
| Inventive Concentrate | 5.0% |
| Citric Acid | 0.5% |
| Dyes, preservatives | Q.S. |
| Total | 100 |
| Diaper Pail Spray-2 | |
| Water | 74.5% |
| Isopropyl Alcohol | 20.0% |
| Inventive Concentrate | 5.0% |
| Citric Acid | 0.5% |
| Dyes, preservatives | Q.S. |
| Total | 100 |
| Diaper Pail Spray-3 | |
| Water | 89.5% |
| Propylene Glycol | 5.0% |
| Inventive Concentrate | 5.0% |
| Citric Acid | 0.5% |
| Dyes, preservatives | Q.S. |
| Total | 100 |
| Disinfectant Cleaner-1 | |
| Water | 91.5% |
| Inventive Concentrate | 5.0% |
| Variquat 80 MC (i.e., a benzalkonium chloride) | 3.0% |
| Citric Acid | 0.5% |
| Dyes, preservatives | Q.S. |
| Total | 100 |
| Disinfectant Cleaner-2 | |
| Water | 91.5% |
| Inventive Concentrate | 5.0% |
| Tegotens DO | 1.7% |
| Variquat 80 MC | 3.0% |
| Citric Acid | 0.5% |
| Dyes, preservatives | Q.S. |
| Total | 100 |
| Disinfectant Cleaner-3 | |
| Water | 34.5% |
| Inventive Concentrate | 5.0% |
| Denatured Ethyl Alcohol | 60.0% |
| Citric Acid | 0.5% |
| Dyes, preservatives | Q.S. |
| Total | 100 |
| Hospital Floor Cleaner-1 | |
| Water | 90.0% |
| Inventive Concentrate | 5.0% |
| Variquat 80 MC | 5.0% |
| Citric Acid | 0.5 % |
| Dyes, preservatives | Q.S. |
| Total | 100 |
| Hospital Floor Cleaner-2 | |
| Water | 93.61% |
| Inventive Concentrate | 3.0% |
| Variquat 80 MC | 3.0% |
| Citric Acid | 0.39% |
| Dyes, preservatives | Q.S. |
| Total | 100 |
| Porta Potty Cleaner-1 | |
| Water | 94.5% |
| Inventive Concentrate | 5.0% |
| Citric Acid | 0.5% |
| Dyes, preservatives | Q.S. |
| Total | 100 |
| Porta Potty Cleaner-2 | |
| Water | 82.25% |
| Inventive Concentrate | 3.3% |
| Rewoteric AMB-14 U | 5.0% |
| Varox 1770 | 5.0% |
| Witcamide 128-T | 2.0% |
| Sodium Chloride | 2.0% |
| Citric Acid | 0.45% |
| Dyes, preservatives | Q.S. |
| Total | 100 |
| Porta Potty Cleaner-3 | |
| Water | 76.0% |
| Inventive Concentrate | 5.0% |
| Rewoteric AM-TEG | 7.0% |
| Phosphoric Acid | 8.0% |
| Sodium Chloride | 4.0% |
| Dyes, preservatives | Q.S. |
| Total | 100 |
| Salon Floor Cleaner | |
| Water | 94.5% |
| Inventive Concentrate | 5.0% |
| Citric Acid | 0.5% |
| Dyes, preservatives | Q.S. |
| Total | 100 |
| Salon Counter Spray | |
| Water | 34.5% |
| Isopropyl Alcohol | 60.0% |
| Inventive Concentrate | 5.0% |
| Citric Acid | 0.5 % |
| Dyes, preservatives | Q.S. |
| Total | 100 |

Each of the above mentioned formulations including the inventive concentrate is exemplary and by no ways limits the scope of the present invention. Instead, the inventive concentrate can be used in any other formulation that is well known to those skilled in the art. Note that the inventive water-soluble concentrate and diluted formulation may be used as a spray, liquid, gel or solid.

The following examples are given to illustrate the present invention and to demonstrate some advantages that can be obtained using the inventive water-soluble concentrate.

EXAMPLE 1

Test Procedure For Cigarette Smoke Odor

Materials:

100-gram samples of the following 3 formulations (Letters a–c) were employed in this example:

a). 0.5 grams of Downy type fragrance in water (several fragrance companies were contacted for fragrances such as: Alpine Aromatics, Arylessence Inc., Givauda-Roure Corp, Aromatics, American Aromatics, Elias Fragrance, Continental Aromatics, International Flavors and Fragrances, Fragrance Resources and H & R Florasynth). A panel was used to smell the different fragrance types each of the companies sent and the unanimous decision was for Arylessence's Downy Fragrance. It was chosen for its appropriate intensity level without being overpowering.

b). 1.6 grams Inventive Concentrate (i.e., blend of 30% zinc ricinoleate and 70% Varonic K-205) in water.

c). 1.6 grams of Inventive Concentrate +0.5 grams of Downy type fragrance in water (Note: 0.25–0.5% citric acid may have been added to formulations containing the Inventive concentrate in order to produce a clear, completely solubilized solution). The Inventive Concentrate is completely solubilized in order to maximize its odor elimination properties.

- 4 pieces of 2" long×4" wide swatches of commercial nylon carpet
- 4 pieces of man-made upholstery fabric
- 8 pieces of cut terry cloth
- 3 pump spray bottles (which formulations were placed in)
- 20 pack of low filtration "Marlboro" cigarettes
- Deionized water for formulations
- Large Dessicator (diameter 410 cm or 9.5 inches) with porcelain tray Procedure:

1). A large strip of commercial nylon carpet was taken and was cut into four 2" long×4" wide swatches.

2). These 4 pieces of carpet were placed on a porcelain tray which contained many holes and the tray was put into an unsealed dessicator.

3). Next one cigarette was chosen and was cut about 1 and ¼ inches from the filter and the cut cigarette was placed under the tray for 5 minutes (until it was completely burned) to burn and fill the carpet with smoke.

4). The carpet was then placed on the bench top for 30 seconds to air out.

5). After the 30 seconds had passed, 3 of the 4 pieces of carpet were each sprayed 5 times with one of the 3 different odor absorption formulations (6 inches from the carpet) and rubbed with a piece of terry cloth. The other piece was left as a control.

6). A panel of people were asked to smell each treated carpet and rate the amount/intensity of odor they could smell on a scale from 0–5, 0 meaning the entire odor was gone and 5 meaning the odor had not been eliminated at all.

7). The same procedure was performed on the upholstery fabric.

Results: The results in Table 1 display how each formulation did on initial contact on the smoke odor present in the carpet in comparison to one another, at the fixed amount of 5 squirts. These results were documented according to the Tour panelists. Table 2 shows the results for upholstery fabric. Note the control sample is a piece of untreated carpet.

TABLE 1

| Initial Contact | Control | Fragrance | Inventive Concentrate | Fragrance + Inventive Concentrate |
|---|---|---|---|---|
| Panelist.1 | 5 | 2 | 3 | 0 |
| Panelist.2 | 5 | 2 | 3 | 0 |
| Panelist.3 | 4 | 2 | 3 | 1 |

TABLE 1-continued

| Initial Contact | Control | Fragrance | Inventive Concentrate | Fragrance + Inventive Concentrate |
|---|---|---|---|---|
| Panelist.4 | 5 | 3 | 2 | 0 |
| Totals | 19 | 9 | 11 | 1 |

TABLE 2

| Initial Contact | Control | Fragrance | Inventive Concentrate | Fragrance + Inventive Concentrate |
|---|---|---|---|---|
| Panelist.1 | 5 | 3 | 3 | 0 |
| Panelist.2 | 5 | 3 | 3 | 0 |
| Panelist.3 | 5 | 2 | 3 | 0 |
| Panelist.4 | 5 | 2 | 3 | 0 |
| Totals | 20 | 10 | 12 | 0 |

Conclusion: The Inventive Concentrate in combination with a suitable fragrance provides malodor performance that is identifiably better than either component alone, but the Inventive Concentrate shows a reduction in malodor as compared to the control sample.

EXAMPLE 2

Test Procedure For Garlic Onion and Fish odor

Materials:

100-gram samples of the following 3 formulations (Letters a–c) were employed:

a). 0.5 grams of Downy type fragrance in water (several fragrance companies were contacted for fragrances such as: Alpine Aromatics, Arylessence Inc., Givauda-Roure Corp, Aromatics, American Aromatics, Elias Fragrance, Continental Aromatics, International Flavors and Fragrances, Fragrance Resources and H & R Florasynth). A panel was used to smell the different fragrance types each of the companies sent and the unanimous decision was for Arylessence's Downy Fragrance. Chosen for its appropriate intensity level without being overpowering.

b). 1.6 grams Inventive Concentrate in water.

c). 1.6 grams of Inventive +0.5 grams of Downy type fragrance in water (Note: 0.25–0.5% Citric acid may have been added to formulations containing the Inventive Concentrate in order to produce a clear, completely solubilized solution). The Inventive Concentrate is completely solubilized in order to maximize its odor elimination properties.

- 18 pieces of 2" long×4" wide swatches of commercial nylon carpet
- 36 pieces of cut terry cloth
- 3 pump spray bottles (which formulations were placed in)
- "Spice World" brand minced garlic
- One large red chopped onion
- "Polar" brand canned chunk light tuna in water
- Deionized water for formulations
- Disposable pipettes (to be used to administer the malodors)

Procedure:

1). A large strip of commercial nylon carpet was employed and the strip was cut into eighteen 2" long×4" wide swatches.

2). Four drops of each malodor one by one (for example garlic was added to 3 swatches then each swatch was treated with a separate odor absorber, this procedure was performed the exact same way for each of the remaining 2 malodors which gave us a total of 9 for "light" malodor treated carpet swatches and 9 for "heavy" malodor treated carpets, which totals 18) in 4 areas of the swatch to obtain a "light" odor. Note: Each malodor was concentrated not diluted with water and was administered directly from their container with a pipette onto the substrate (carpet).

3). The carpet was then rubbed with a terry cloth for 30 seconds and left to sit for 5 minutes.

4). After the 5 minutes had passed each carpet swatch was sprayed once with the 3 different odor absorption formulations 6 inches from the carpet.

5). Next a panel of people were asked to smell each treated carpet and rate the amount/intensity of odor they could smell on a scale from 0–5, 0 meaning the entire odor was gone and 5 meaning the odor had not been eliminated at all.

6). If the odor was still smelled by the panelists the carpet was continuously sprayed with the odor absorber one spray at a time until the odor was eliminated.

7). This same procedure above was repeated with 10 drops of the malodors to obtain a "heavy" odor.

Results: The results given in Table 3 display the amounts of each odor absorber formulation needed to completely eliminate the odor.

TABLE 3

|  | Fragrance | Inventive Concentrate | Fragrance + Inventive Concentrate |
|---|---|---|---|
| Garlic "Light" | 2 | 1 | 1 |
| Garlic "Heavy" | 5 | 4 | 2 |
| Onion "Light" | 3 | 3 | 1 |
| Onion "Heavy" | 3 | 5 | 2 |
| Tuna Fish "Light" | 7 | 7 | 2 |
| Tuna Fish "Heavy" | 9 | 20 | 9 |

Conclusion: The Inventive Concentrate in combination with a suitable fragrance will provide malodor performance that is identifiably better than either component alone.

While the present invention has been particularly shown and described with respect to preferred embodiments thereof, it will be understood by those skilled in the art that the foregoing and other changes in form and detail may be made without departing from the spirit and scope of the present invention. It is therefore intended that the present invention not be limited to the exact forms described and illustrated, but fall within the scope of the present claims.

What is claimed is:

1. A water-soluble concentrate comprising a melt blend consisting essentially of zinc ricinoleate and at least one alkoxylated amine having the formula $R(nAO)_sNH_t$, wherein R is a saturated or unsaturated, linear or branched alkyl containing from 8 to 22 carbon atoms; AO is a $C_2$–$C_6$ alkoxylate; n is the number of moles of AO and is from 1 to 50; s=1, 2 or 3; t=0, 1 or 2; and the sum of s and t is 3.

2. The water-soluble concentrate of claim 1 wherein said zinc ricinoleate is prepared by reacting a zinc salt with ricinoleic acid and esterifying the reaction product thereof.

3. The water-soluble concentrate of claim 1 wherein said alkoxylated amine comprises a $C_2$–$C_4$ coco or tallow amine having 2–10 moles of AO.

4. The water-soluble concentrate of claim 3 wherein said alkoxylated amine is ethoxylated tallow amine having 10 moles of ethoxylate (EO).

5. The water-soluble concentrate of claim 3 wherein said alkoxylated amine is an ethoxylated coco amine having 5 moles of EO.

6. A diluted water-soluble formulation comprising:
(a) from about 1 to about 50 weight % of a melt blend consisting essentially of zinc ricinoleate and at least one alkoxylated amine having the formula $R(nAO)_sNH_t$, wherein R is a saturated or unsaturated, linear or branched alkyl containing from 8 to 22 carbon atoms; AO is a $C_2$–$C_6$ alkoxylate; n is the number of moles of AO and is from 1 to 50; s=1, 2 or 3; t=0, 1 or 2; and the sum of s and t is 3; and
(b) from about 50 to 90 weight % of at least one solvent, wherein said at least one solvent is capable of solubilizing said blend into a diluted formulation that contains about 20%, by weight, or greater activated zinc atoms which are capable of binding with malodor molecules.

7. The diluted water-soluble formulation of claim 6 wherein from about 1 to about 10 weight % of said blend and from about 90 to about 99 weight % of said at least one solvent is present.

8. The diluted water-soluble formulation of claim 6 wherein said at least one solvent is selected from the group consisting of water, carboxylic acids, carboxylic acid salts and mixtures thereof.

9. The diluted water-soluble formulation of claim 8 wherein said at least one solvent is water.

10. The diluted water-soluble formulation of claim 8 wherein said at least one solvent is a mixture of water and citric acid.

11. The diluted water-soluble formulation of claim 8 wherein said at least one solvent is a mixture of water and lactate acid.

12. The diluted water-soluble formulation of claim 6 wherein said diluted formulation contains 30%, by weight, or greater of said activated zinc atoms.

13. The diluted water-soluble formulation of claim 6 wherein said zinc ricinoleate is prepared by reacting a zinc salt with ricinoleic acid and esterifying the reaction product thereof.

14. The diluted water-soluble formulation of claim 6 wherein said alkoxylated amine comprises a $C_2$–$C_4$ alkoxylated coco or tallow amine having 2–10 moles of AO.

15. The diluted water-soluble formulation of claim 14 wherein said alkoxylated amine is an ethoxylated tallow amine having 10 moles of EO.

16. The diluted water-soluble formulation of claim 14 wherein said alkoxylated amine is an ethoxylated coco amine having 5 moles of EO.

17. The diluted water-soluble formulation of claim 6 further comprising an additional formulating agent.

18. The diluted water-soluble formulation of claim 17 wherein said additional formulating agent comprises anionic surfactants, ionic surfactants, amphoteric surfactants, zwitterionic surfactants, additional solvents, dyes, preservatives, emulsifying agents, perfumes, antibacterial agents, thickeners, conditioners, antistatic agents, silicone surfactants or any mixtures and combinations thereof.

19. A method of preparing a water-soluble concentrate comprising the steps of:
(a) providing a mixture consisting essentially of zinc ricinoleate and at least one alkoxylated amine having the formula $R(nAO)_sNH_t$, wherein R is a saturated or unsaturated, linear or branched alkyl containing from 8 to 22 carbon atoms; AO is a $C_2$–$C_6$ alkoxylate; n is the number of moles of AO and is from 1 to 50; s=1, 2 or 3; t=0, 1 or 2; and the sum of s and t is 3; and (b) heating the mixture to a temperature that is above the melting point of the zinc ricinoleate.

20. The method of claim 19 wherein step (a) comprises adding said alkoxylated amine to said zinc ricinoleate.

21. The method of claim 20 wherein from about 150 to about 400 grams of said alkoxylated amine is added to 100 gms of said zinc ricinoleate.

22. The method of claim 21 wherein from about 185 to about 300 grams of said alkoxylated amine is added to 100 gms of said zinc ricinoleate.

23. The method of claim 20 wherein said alkoxylated amine comprises a $C_2$–$C_4$ alkoxylated coco or tallow amine having 2–10 moles of AO.

24. The method of claim 23 wherein said alkoxylated amine is an ethoxylated tallow amine having 10 moles of EO.

25. The method of claim 23 wherein said alkoxylated amine is an ethoxylated coco amine having 5 moles of EO.

26. The method of claim 19 wherein step (b) is preformed at a temperature of from about 40° to about 80° C. for a time period of from about 10 to about 60 minutes.

27. The method of claim 26 wherein step (b) is preformed at a temperature of from about 50° to about 70° C. for a time period of from about 20 to about 30 minutes.

28. A method for preparing a diluted water-soluble formulation comprising the steps of:
   (a) providing a concentrated melt blend consisting essentially of a zinc ricinoleate and at least one alkoxylated amine; and
   (b) adding at least one solvent to said concentrated zinc ricinoleate/alkoxylated amine blend, wherein said at least one solvent is capable of solubilizing said blend into a diluted formulation that contains about 20%, by weight, or greater activated zinc atoms.

29. The method of claim 28 wherein step (a) comprises an addition step and a heating step.

30. The method of claim 29 wherein the addition step comprises adding from about 150 to about 400 grams of said alkoxylated amine is added to 100 grams of said zinc ricinoleate.

31. The method of claim 30 wherein from about 185 to about 300 grams of said alkoxylated amine is added to 100 gms of said zinc ricinoleate are employed in said addition step.

32. The method of claim 29 wherein said heating step is preformed at a temperature of from about 40° to about 80° C. for a time period of from about 10 to about 60 minutes.

33. The method of claim 32 wherein heating step is preformed at a temperature of from about 50° to about 70° C. for a time period of from about 20 to about 30 minutes.

34. The method of claim 28 wherein said alkoxylated amine comprises a $C_2$–$C_4$ alkoxylated coco or tallow amine having 2–10 moles of AO.

35. The method of claim 34 wherein said alkoxylated amine is an ethoxylated tallow amine having 10 moles of EO.

36. The method of claim 34 wherein said alkoxylated amine is an ethoxylated coco amine having 5 moles of EO.

37. The method of claim 28 wherein said at least one solvent is selected from the group consisting of water, carboxylic acids, carboxylic acid salts and mixtures thereof.

38. The method of claim 37 wherein said at least one solvent is water.

39. The method of claim 37 wherein said at least one solvent is a mixture of water and citric acid.

40. The method of claim 39 wherein said at least one solvent is a mixture of water and lactate acid.

41. The method of claim 28 where from about 100 to about 10,000 ml of said solvent is added to 100 ml of said concentrated zinc ricinoleate/alkoxylated amine blend.

42. The method of claim 41 where from about 1000 to about 3000 ml of said solvent is added to 100 ml of said concentrated zinc ricinoleate/alkoxylated amine blend.

* * * * *